United States Patent
Yassinzadeh et al.

(10) Patent No.: US 10,660,627 B2
(45) Date of Patent: *May 26, 2020

(54) APPARATUS AND METHODS FOR ACCESSING AND CLOSING MULTIPLE PENETRATIONS ON A BLOOD VESSEL

(71) Applicant: Cardiva Medical, Inc., Santa Clara, CA (US)

(72) Inventors: Zia Yassinzadeh, San Jose, CA (US); John L. Russell, Shoreview, MN (US); Justin L. Ballotta, Oakland, CA (US)

(73) Assignee: Cardiva Medical, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/704,571

(22) Filed: Dec. 5, 2019

(65) Prior Publication Data

US 2020/0107822 A1    Apr. 9, 2020

Related U.S. Application Data

(63) Continuation of application No. 16/002,996, filed on Jun. 7, 2018, now Pat. No. 10,531,868.

(Continued)

(51) Int. Cl.
*A61B 17/08* (2006.01)
*A61B 17/00* (2006.01)
*A61B 90/00* (2016.01)

(52) U.S. Cl.
CPC .......... *A61B 17/0057* (2013.01); *A61B 90/39* (2016.02); *A61B 2017/00004* (2013.01); *A61B 2017/0061* (2013.01); *A61B 2017/0065* (2013.01); *A61B 2017/00592* (2013.01); *A61B 2017/00623* (2013.01); *A61B 2017/00637* (2013.01); *A61B 2017/00672* (2013.01); *A61B 2017/00676* (2013.01);

(Continued)

(58) Field of Classification Search
CPC ... A61B 17/08; A61B 17/10; A61B 17/12022; A61B 17/0057; A61B 2017/00623; A61B 2017/00637; A61B 2017/00654; A61B 2017/00659; A61B 2017/00592
See application file for complete search history.

(56) References Cited

U.S. PATENT DOCUMENTS 5,275,616 A * 1/1994 Fowler ............... A61B 17/0057
                                              604/15
7,025,776 B1 * 4/2006 Houser ............... A61B 17/0057
                                              606/213

* cited by examiner

*Primary Examiner* — Vi X Nguyen
(74) *Attorney, Agent, or Firm* — Wilson Sonsini Goodrich & Rosati

(57) ABSTRACT

Multiple vascular wall penetrations are formed and sealed in a single blood vessel, typically a vein, for performing cardiac and other catheter-based procedures. Access sheaths are placed in two or more tissue tracts each having a vascular wall penetration at a distal end and into a lumen of the blood vessel. A catheter is advanced though each of the access sheaths to perform a therapeutic or diagnostic procedure. A vascular closure device is introduced through each access sheath, typically sequentially, and an occlusion element at a distal end of the device is deployed against an inner wall of the blood vessel in a manner so that the adjacent access sheath does not interfere or overlap with the deployed occlusion element. The vascular penetration at the distal end in that tissue tract may then be sealed prior to using another vascular closure device to seal a caudally adjacent vascular wall penetration.

36 Claims, 17 Drawing Sheets

Related U.S. Application Data

(60) Provisional application No. 62/593,728, filed on Dec. 1, 2017.

(52) U.S. Cl.
CPC ... *A61B 2090/376* (2016.02); *A61B 2090/378* (2016.02); *A61B 2090/3925* (2016.02); *A61B 2090/3966* (2016.02)

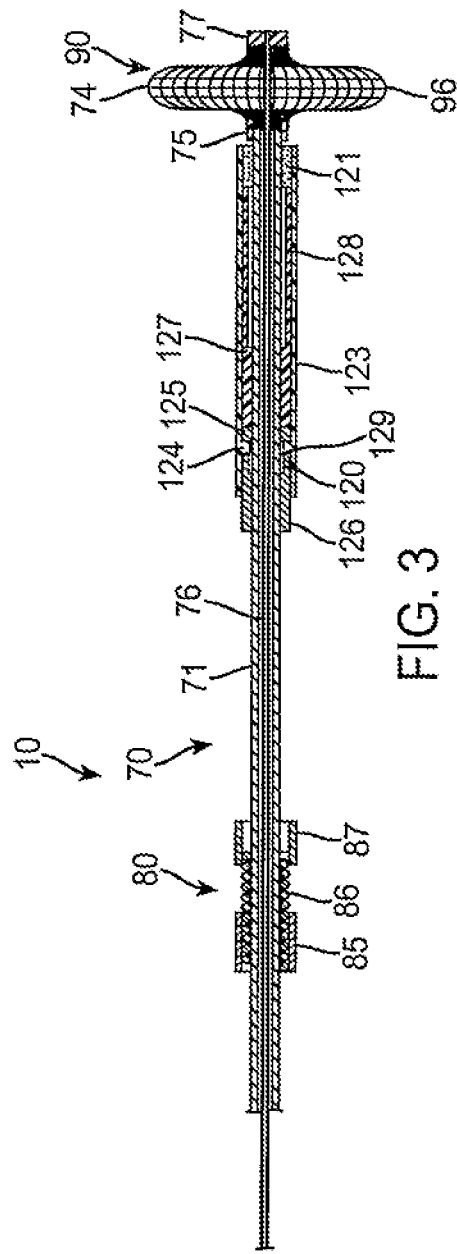
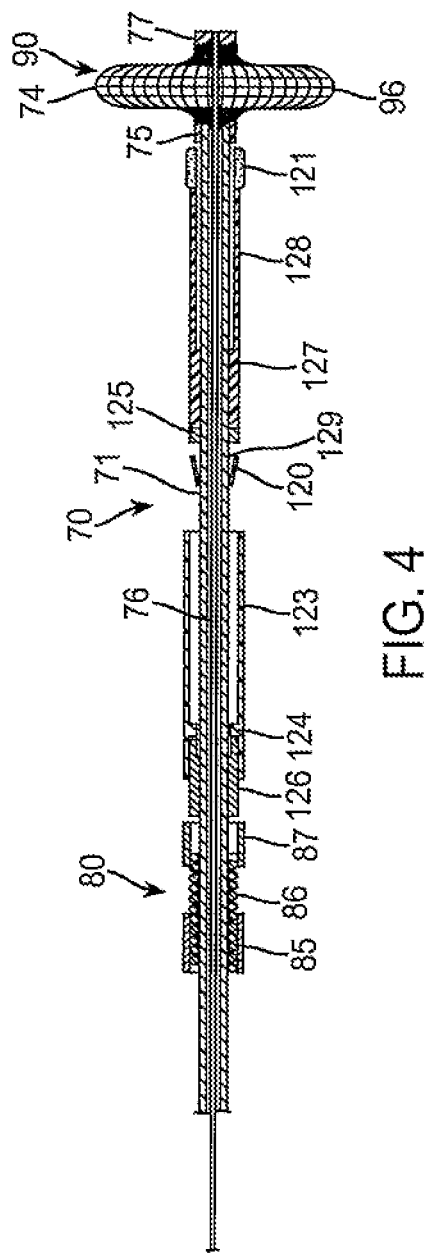

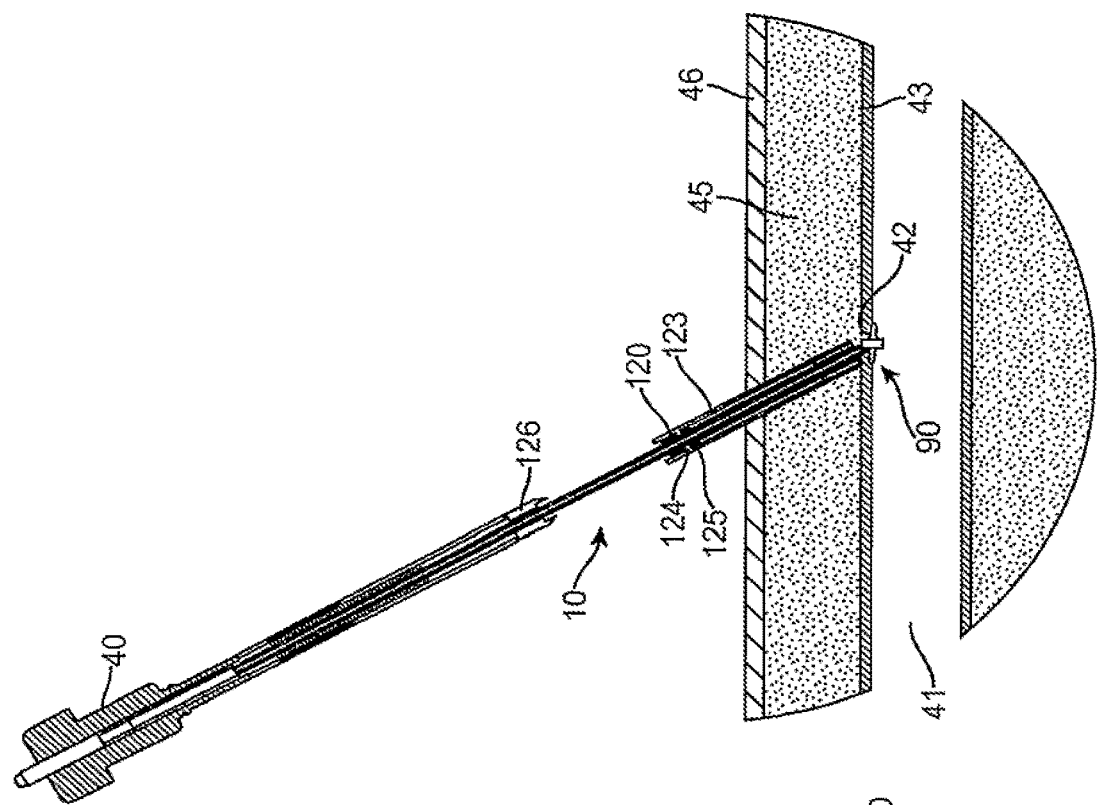
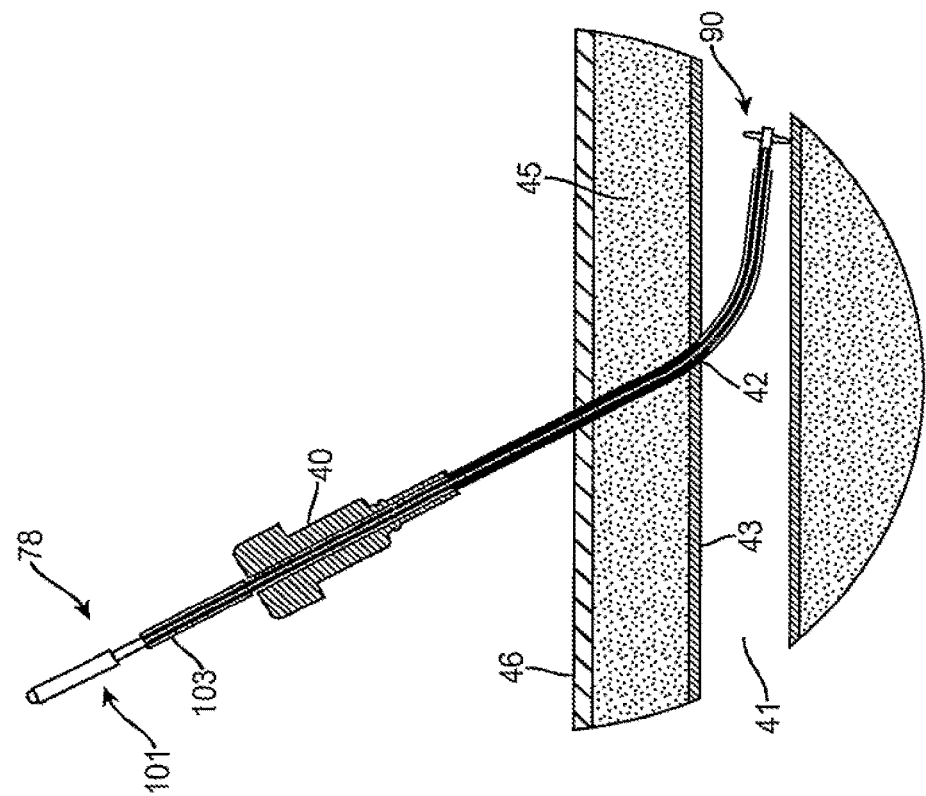

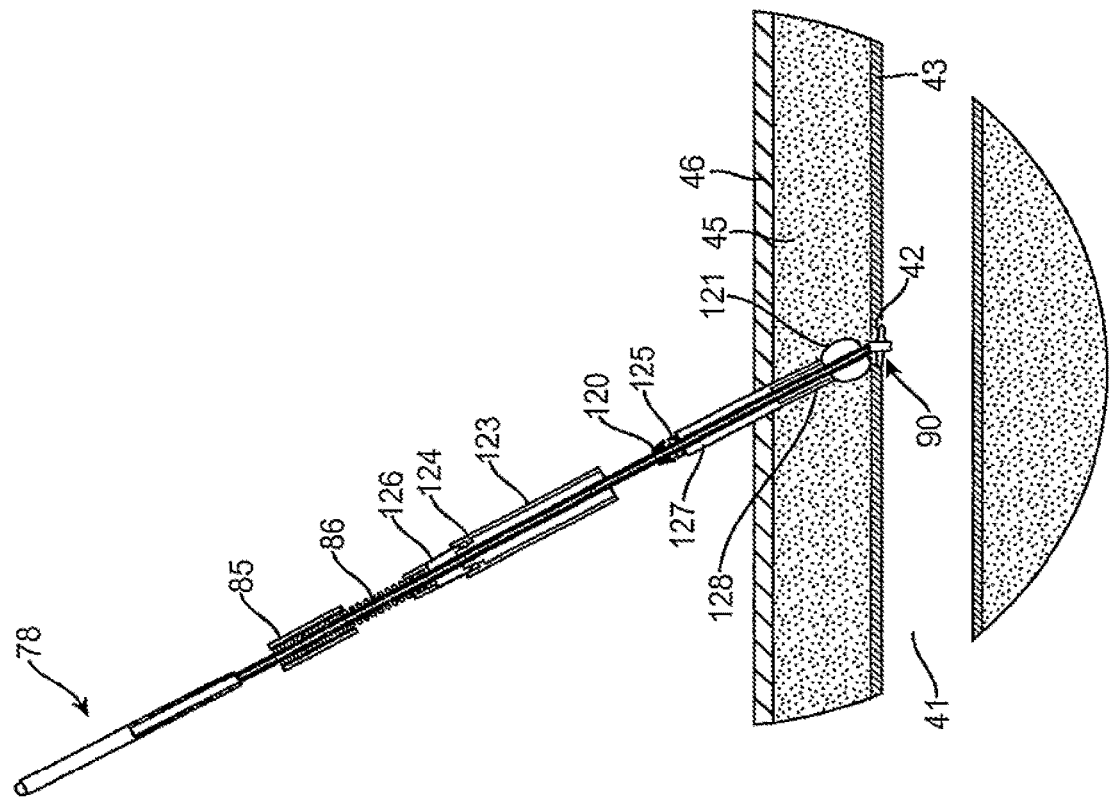
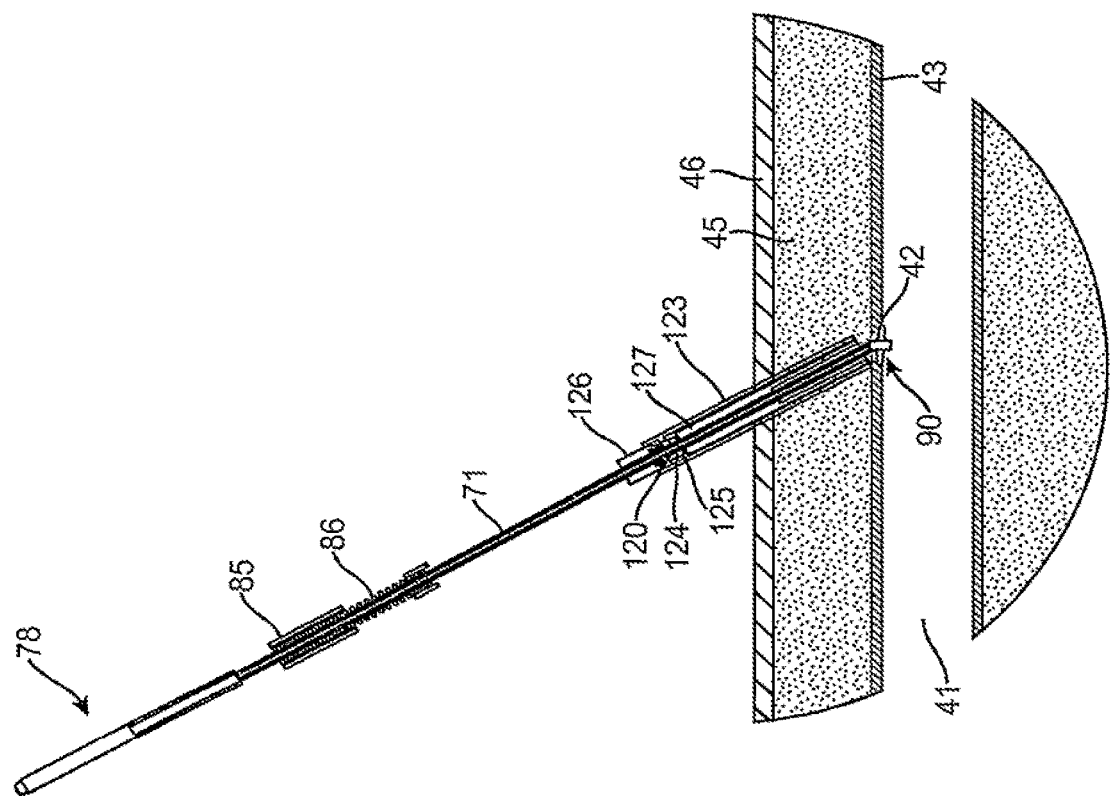

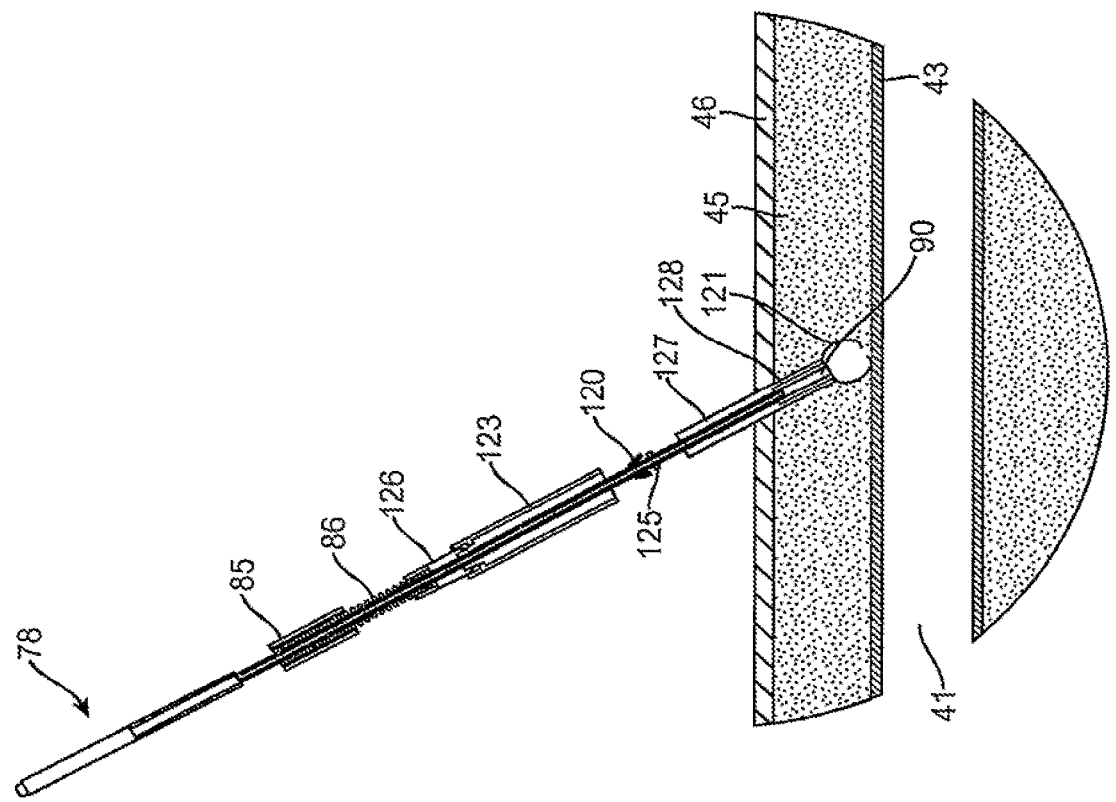
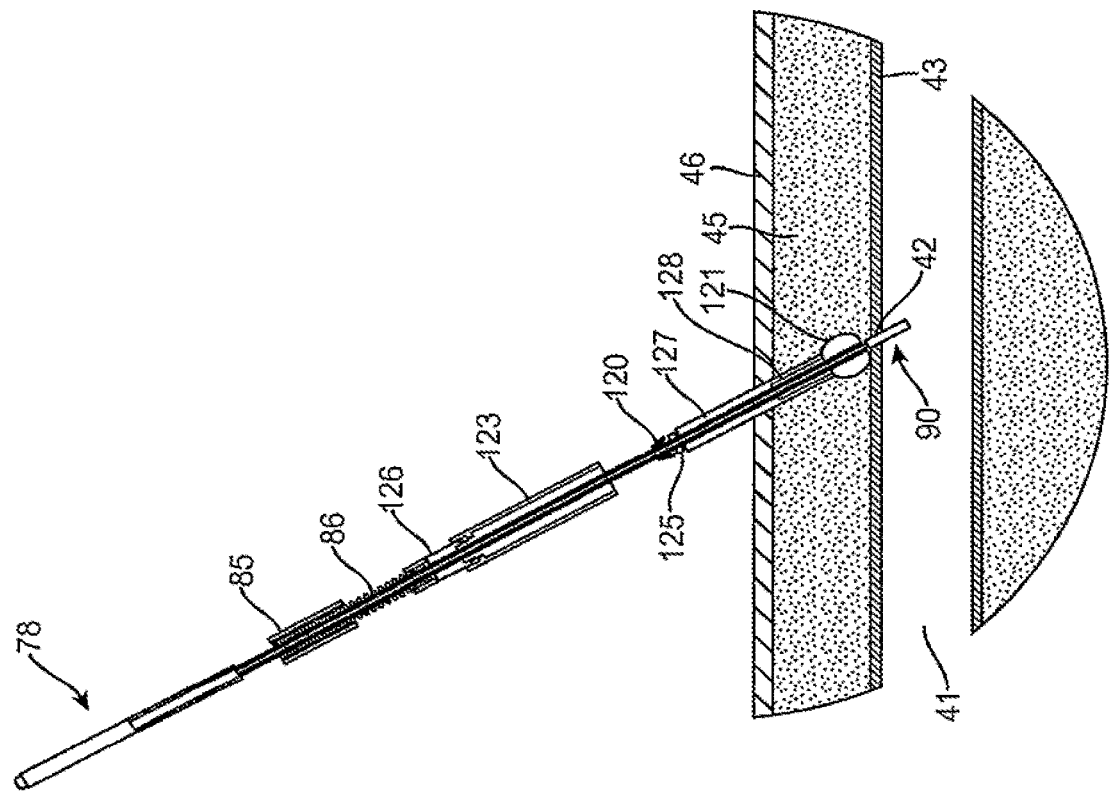

APPARATUS AND METHODS FOR ACCESSING AND CLOSING MULTIPLE PENETRATIONS ON A BLOOD VESSEL

CROSS-REFERENCES TO RELATED APPLICATIONS

This application is a continuation of U.S. patent application Ser. No. 16/002,996, filed Jun. 7, 2018, now U.S. Pat. No. 10,531,868, which claims the benefit of provisional patent application 62/593,728, filed on Dec. 1, 2017, the full disclosures of which are incorporated herein by reference.

The disclosure of the present application contains common subject matter with application Ser. No. 13/452,656, now U.S. Pat. No. 8,911,472, filed on Apr. 20, 2012, and with application Ser. No. 14/542,066, filed on Nov. 14, 2014, now U.S. Pat. No. 9,439,637, the full disclosures of which are incorporated herein by reference.

BACKGROUND OF THE INVENTION

1. Field of the Invention

The present invention relates generally to medical devices and methods. More particularly, the present invention relates to apparatus and protocols for closing arteriotomies, venotomies, and other vascular wall penetrations.

Angiography, angioplasty, atherectomy, cardiac ablation, and a number of other vascular and cardiovascular procedures are performed intravascularly and require percutaneous access into the patient's vasculature, including both the arterial and venous vasculature. The most common technique for achieving percutaneous access is called the Seldinger technique, where access to a blood vessel, typically a femoral artery or vein in the groin, is first established using a needle to form a "tract," i.e., a passage through the tissue overlying the blood vessel. The needle tract is then dilated, and an access sheath is placed into the dilated tract and through a penetration in the vascular wall, such as an arteriotomy to allow the introduction of guidewires, interventional catheters, catheter exchange, and the like, through the indwelling access sheath to perform the desired procedure.

Once the desired procedure is completed, the access sheath must be removed and the arteriotomy or other vascular wall penetration closed. For many years, such closure was achieved by applying manual pressure onto the patient's skin over the site of the vascular wall penetration. Patients, however, have often been heparinized to limit the risk of thrombosis during the procedure, and clotting of the vascular wall penetration can often take an extended period, particularly when the penetration is relatively large for performing procedures needing larger diameter catheters. For these reasons, a number of vascular closure devices have been developed and commercialized which provide for closure of a vascular wall penetration, typically by placing a resorbable collagen plug in the tissue tract immediately above the penetration.

Exemplary closure devices include the Vascade® and Cardiva Catalyst® vascular closure systems available from Cardiva Medical, Inc., assignee of the present application. Both these systems include an expansible element at a distal tip of a shaft for providing temporary hemostasis when placed in the blood vessel adjacent to the vascular wall penetration. The Vascade® system includes a hemostatic plug which can be placed in the tissue tract, allowing the shaft to be immediately withdrawn, while the Cardiva Catalyst® system is coated with catalytic material which induces clotting over time, requiring that the device shaft be left in place for some time after deployment of the expansible element. The construction and use of these system are described, for example, in commonly owned U.S. Pat. Nos. 7,691,127 and 9,179,897, the full disclosures of which are incorporated herein by reference.

Of particular interest to the present invention, cardiac ablation and other procedures have been developed which require the introduction of two, three, four, and possibly even more individual catheters through a single blood vessel, usually a vein in the case of cardiac ablation, for performing a procedure. Such introduction of multiple catheters, in turn, requires the introduction of multiple access sheaths and the consequent need for the closure of multiple vascular access penetrations.

As with other vascular closure protocols, it would be advantageous to close multiple penetrations in a single access vessel using the Vascade® system, the Cardiva Catalyst® system or other closure systems which leave minimal or no material permanently behind. Despite the success of the Vascade® system, the Cardiva Catalyst® system, and other vascular closure systems in closing single penetrations, when closing multiple vessel penetrations in a single vessel, the closure devices can interfere with each other. In addition to physical interference, the presence of multiple access sheaths and/or multiple closure catheters can also limit the ability to properly image the closure site to confirm proper placement of the closure catheters and associated seals.

For these reason, it would be desirable to provide improved protocols for closing and sealing multiple venotomies, arteriotomies and other vascular wall penetrations, where the closure may be achieved with the use of multiple vascular closure catheters, frequently in presence of an indwelling sheath, with minimum or no interference. At least some of these objectives will be met by the inventions described below.

2. Background of the Invention

U.S. Pat. Nos. 7,691,127 and 9,179,897, have been described above. U.S. Pat. No. 7,335,219 describes a device for delivering a plug of hemostatic material to a location just above a blood vessel wall penetration. The hemostatic material is encapsulated in a dissolvable structure and a non-expandable control tip assembly helps advance the device through the tissue tract and may also provide hemostasis and bleed back. US 2007/0123817 and U.S. Pat. No. 7,008,439 describe apparatus for sealing a vascular wall penetration. Other apparatus for closing blood vessel wall punctures are described in U.S. Pat. Nos. 4,744,364; 5,061,271; 5,728,133; and 7,361,183 and U.S. Published Patent Application Nos. 2003/0125766; 2004/0267308; 2006/0088570; 2007/0196421; and 2007/0299043. The incorporation of anti-proliferative materials in hemostatic materials for blood vessel closure and other purposes is described in U.S. Pat. Nos. 7,025,776 and 7,232,454; 6,554,851; and U.S. Published Patent Application Nos. 2005/0004158; 2005/0038472; 2007/0060895/2007/0032804; and 2008/0039362.

BRIEF SUMMARY OF THE INVENTION

The present invention provides a method for forming and sealing a plurality of access penetrations in a blood vessel. Two or more tissue tracts, including at least a cephalad-most and a caudal-most tissue tract, each having a vascular wall penetration at a distal end thereof, are formed from a skin surface to an access blood vessel, either an artery or a vein, but usually a femoral vein for cardiac access by multiple catheters. An access sheath is placed through each tissue tract and associated vascular wall penetration and enters into a lumen of the access blood vessel. A therapeutic or diagnostic catheter is advanced though each of the indwelling access sheaths, and the catheters are used to perform a therapeutic or diagnostic procedure. After the procedure is completed, a plurality of vascular closure devices, each device including a shaft and an occlusion element at a distal end of the shaft, are used to seal the vascular wall penetrations. One shaft of each device is advanced through each access sheath and tissue tract to position the occlusion element of the device in the lumen of the blood vessel. The occlusion element, a releasable anchor or a radially expandable element, is deployed and engaged against an inner wall of the blood vessel. The radially expandable element, typically an elastomeric disc but alternatively an inflatable balloon or other radially expandable occlusion element, is expanded to a width sufficient to inhibit blood flow through the vascular wall penetration into the tissue tract. The tissue tracts are initially oriented and located so that (a) adjacent occlusion elements, when deployed simultaneously within the blood vessel, do not overlap with each other and (b) the occlusion element does not overlap or otherwise interfere with an adjacent indwelling sheath, when each vascular penetration is sealed first, prior to deploying a closure device in an adjacent access sheath within the same vessel.

In specific aspects, the two or more tissue tracts are formed along parallel paths from a skin surface to the blood vessel. The parallel paths have a minimum spacing along a cephalad-caudal axis equal to the sum of (1) one-half of a deployed length or diameter of the occlusion element and (2) one-half a diameter of the access sheath, or if more than one closure device is to reside in the vessel, the parallel paths may be spaced-apart along the cephalad-caudal axis by at least a full length or a full diameter of the occlusion element. Typically, tracts are spaced-apart by a distance in the range from 0.5 cm to 2 cm, often from 0.5 cm to 1.5 cm. The blood vessel may be a femoral vein, typically for cardiac access, and the parallel paths are deployed at an acute angle relative to the upstream segment of the femoral vein at the point of vascular penetration, toward the patient's feet (i.e., in a caudal direction relative to the vascular wall penetration). The acute angle is usually in a range from 30° to 60°. In situations where the closure device is used in presence of other sheaths, for improved imaging and better visibility, the vascular closure devices are typically placed in an order, beginning with the most proximal or cephalad (toward the head) vascular penetration, and continuing toward more caudal position next. In this way, the closure device in use will generally lie over any adjacent indwelling sheaths and will thus not be masked by them during fluoroscopy and/or or ultrasound imaging for disc placement confirmation. This allows confirmation that the disc is properly placed against the intima and the hemostatic implant is properly placed in the tissue tract and not in the vasculature. In particular examples, the therapeutic or diagnostic procedure may comprise a cardiac procedure, e.g., at least one of cardiac mapping and ablation.

In specific embodiments, the vascular wall penetration in a cephalad-most tissue tract is first sealed and the first vascular closure device withdrawn prior to introducing the shaft of a second vascular closure device into a second caudally adjacent access sheath. The vascular wall penetration in the second caudally adjacent tissue tract may then be sealed using a second vascular wall closure device which can be imaged without interference from presence of the first vascular closure device and first access sheath, both of which have been removed. After sealing the second vascular wall penetration, the second vascular closure device is withdrawn prior to introducing the shaft of a third vascular closure device into a third access sheath caudally adjacent the second vascular wall penetration. The vascular wall penetration in the third caudally adjacent tissue tract is sealed, and the third vascular closure device is withdrawn prior to introducing the shaft of a fourth vascular closure device into a fourth caudally adjacent access sheath. In each of these cases, sealing typically comprises releasing a hemostatic plug from the shaft of the vascular closure device over the vascular wall penetration at the distal end of the tissue tract.

In yet another embodiment, all closure devices may be placed before performing any of the sealing steps, starting with the cephalad-most tissue tract and removal of the access sheath, and continuing in the caudal direction. The fluoroscopic or ultrasonic imaging of all devices in the vessel may then be conducted. Once it is confirmed that the devices are properly placed, the access sites may be sealed.

In still further particular embodiments, the cephalad-most vascular closure device is fluoroscopically or ultrasonically imaged such that there are no access sheaths on a cephalad side of the imaged vascular closure device to interfere with the image. Withdrawal of a cephalad-positioned access sheath exposes a caudally adjacent access sheath and vascular closure device for fluoroscopic imaging.

BRIEF DESCRIPTION OF THE DRAWINGS

FIGS. 3-7 illustrate the further steps of deployment of the hemostatic implant from the apparatus of FIGS. 1 and 2.

FIGS. 8A-8I illustrate placement and deployment of the hemostatic implant using the apparatus of FIGS. 1 and 2 through a vascular sheath placed in a blood vessel.

DETAILED DESCRIPTION OF THE INVENTION

Figure 1:
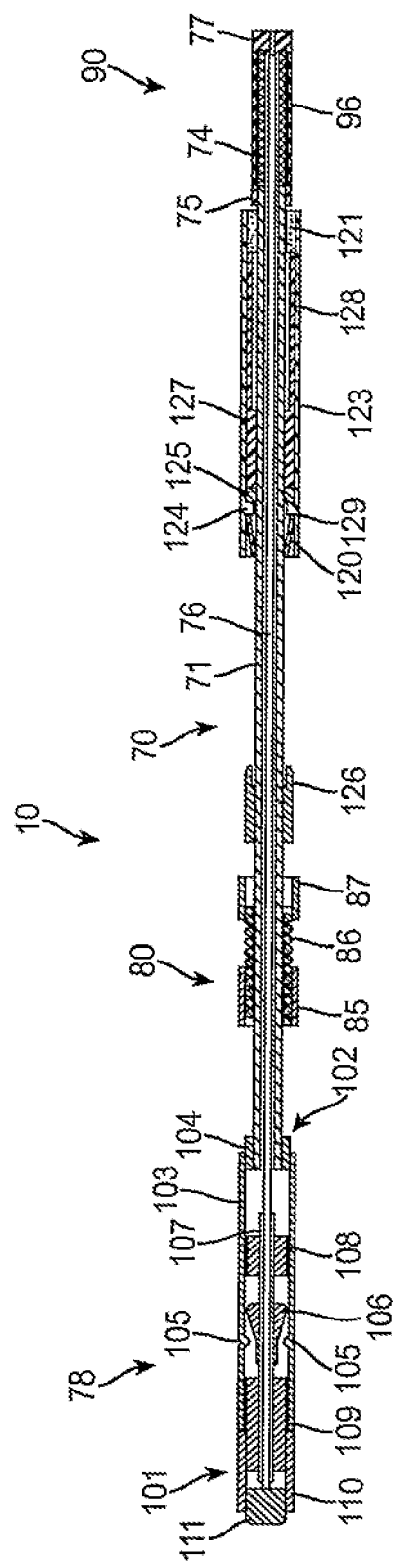
FIG. 1 illustrates an exemplary sealing apparatus constructed in accordance with the principles of the present invention, shown in section.
Figure 1A:
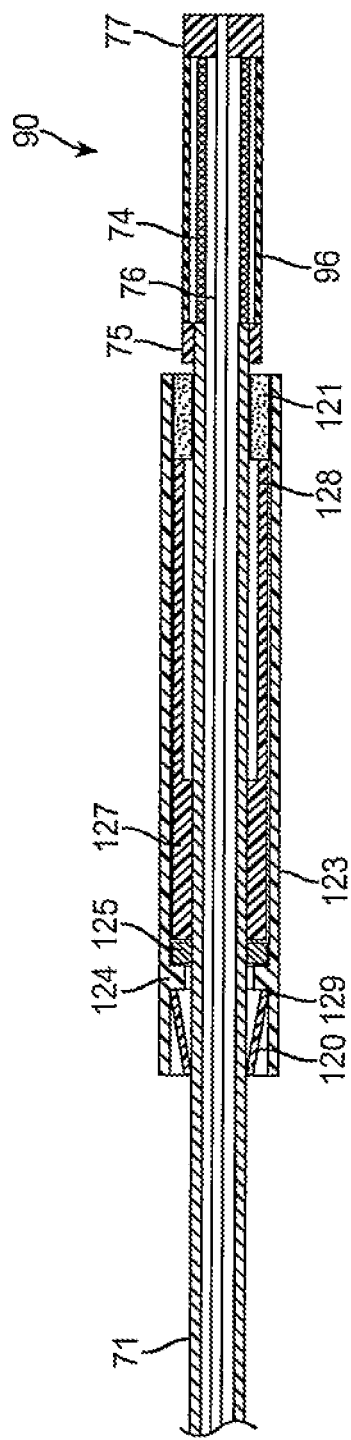
FIG. 1A is a detailed view of a distal portion of the sealing apparatus of FIG. 1, shown in partial section.

Referring to FIGS. 1 and 1A, an exemplary sealing apparatus 10 constructed in accordance with the principles of the present invention comprises a shaft assembly 70 including an outer tube 71 and an inner rod 76. An expansible occlusion element 90 is mounted at a distal end (to the right in FIGS. 1 and 1A) of the shaft assembly 70 and includes a radially expansible mesh 74 covered by an elastomeric membrane 96. A handle assembly 78 is attached to a proximal end of the shaft assembly 70 and is operatively attached to both the outer tube 71 and inner rod 76 so that the inner rod can be axially advanced and retracted relative to the outer tube. The inner rod 76 and outer tube 71 are coupled together at the distal tip of the sealing apparatus 10 by a plug 77 and a proximal anchor 75, respectively. The occlusion element 90 is held between the plug 77 and the proximal anchor 75 so that axial retraction of the rod in the proximal direction (to the left as shown in FIGS. 1 and 1A) foreshortens the occlusion element 90, causing the occlusion element to expand radially, as shown for example in FIG. 2. The plug 77 and anchor 75 may be fabricated at least partly from radiopaque materials, such as nitinol, to provide means to fluoroscopically verify the location of the expansible occlusion member 90 against the vessel wall. Confirming the location of the deployed expansible occlusion member is particularly useful prior to release of a hemostatic implant 121, e.g., to avoid accidental release of the implant into the vessel lumen.

Figure 2:
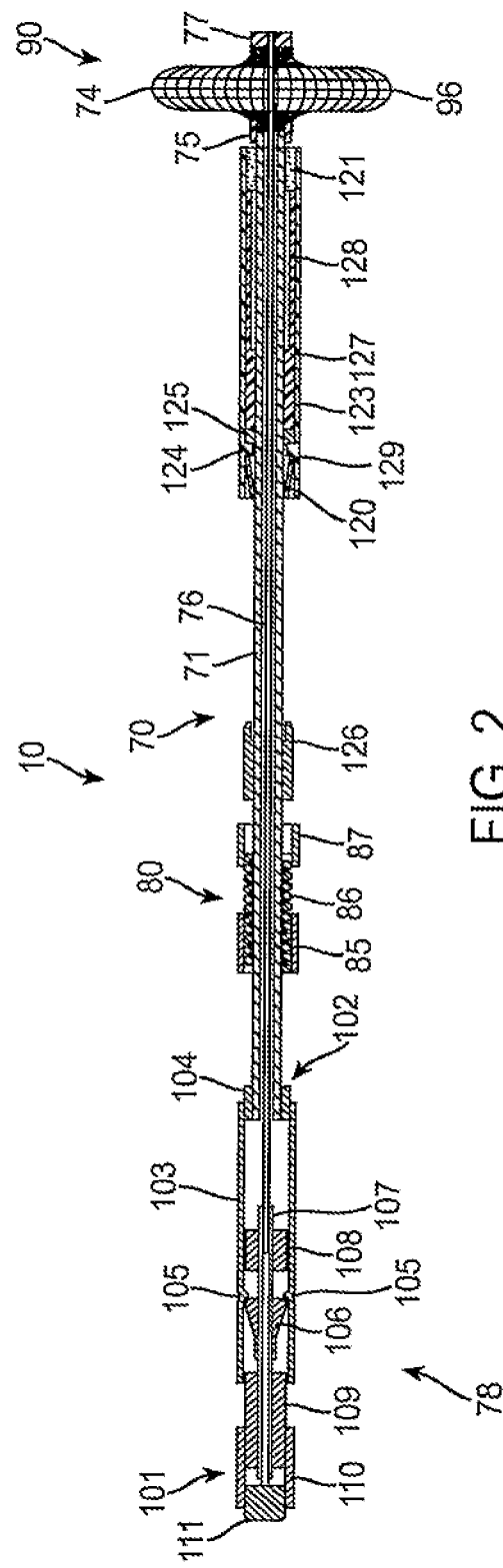
FIG. 2 is a cross-sectional view of the sealing apparatus of FIG. 1, shown with an expanded occlusion element.

Axial advancement and retraction of the rod 76 relative to the outer tube 71 is effected using the handle assembly 78. The handle assembly 78 includes a cylindrical body 103 attached to the proximal end of the outer tube 71 by a bushing 104 so that the body 103 will remain fixed relative to the outer tube as the inner rod 76 is retracted and advanced. The inner rod is retracted and advanced by a slide assembly 101 which includes a short tube 110 fixedly attached to an endcap 111 and a slide cylinder 109. The inner rod 76 is secured by tube element 107 which carries locking element 106 and bearing elements 108 and 109. Bearing element 109 is attached to proximal grip 101 and the assembly of the grip 101 and tube element 107 can slide freely within the interior of the cylindrical body 103 so that the rod 76 may be proximally retracted relative to the body 103 and outer tube 71, as shown in FIG. 2. Once the expansible occlusion element 90 has been radially expanded, the rod 76 will remain retracted and is held in place by locking element 106 which is pulled over a detent 105, again as shown in FIG. 2. An alignment bushing 108 is provided in the interior of the cylindrical body 103 to maintain alignment of the slide assembly 101 relative to the cylindrical body.

The sealing apparatus of the present invention may optionally include a tensioning mechanism 80 which includes a coil spring 86, a gripping element 85, and a coupling element 87. The tensioning mechanism 80 may be selectively positioned along the length of shaft assembly 70, and will provide a tension determined by the constant of coil spring 86 to hold the expanded occlusion element 74 against the vascular penetration, as described in more detail in copending, commonly-owned application Ser. No. 10/974,008, the full disclosure of which is incorporated herein by reference. As described thus far, the construction and use of the sealing apparatus including shaft assembly 70, handle assembly 78, tensioning mechanism 80, and expansible occlusion element 90 are generally the same as illustrated in copending application Ser. No. 10/974,008. The present invention is directed at modifications and improvements to the earlier device for delivering a hemostatic implant into the tissue tract generally above the vascular wall penetration, as will be described in more detail below.

As best seen in FIG. 1A, hemostatic implant 121, which will typically be a biodegradable polymer, is carried coaxially or in parallel over the outer tube 71 near the distal end thereof proximal to the expansible occlusion element 90. While the hemostatic implant 121 is shown to be positioned coaxially over outer tube 71 in FIG. 1A, it will often be desirable to modify or reposition the implant in order to facilitate release from the sealing apparatus after the implant has been deployed. More simply, the hemostatic implant could be axially split to allow it to partially open after it is hydrated and facilitate passage of the collapsed occlusion element 74 as the sealing apparatus is being withdrawn. Alternatively, the hemostatic implant may be reconfigured and carried laterally (i.e., to one side of) with respect to the shaft of the sealing apparatus, as described in more detail hereinafter with respect to FIGS. 9A and 9C. The hemostatic implant 121 could alternatively be carried on the inner surface of a protective sleeve 123 which is slidably carried over the outer tube 71. The protective sleeve 123 slides over a backstop 127 which is slidably mounted over the outer tube 71 and which is prevented from moving proximally by stop member 125 which is fixed to the outer surface of the outer tube. Backstop 127 has a distal end 128 which engages a proximal end of the hemostatic implant 121. Thus, by proximally retracting the protective sleeve 123, the hemostatic implant 121 can be exposed to the tissue tract and released from the sealing apparatus.

Accidental axial retraction of the protective sleeve 123 is prevented by a latch mechanism including a latch element 120 and a key 126 (FIGS. 1 and 2). The latch element 120 is typically a spring-loaded component, for example a conical spring having a narrow diameter end attached to the outer tube 71 and a flared or larger diameter end 129 which engages a stop ring 124 formed on the inner surface of the protective sleeve 123. So long as the flared end 129 of the latch element 120 remains in its flared or open configuration, as illustrated in FIG. 1A, accidental proximal retraction of the sleeve is prevented. It is further noted that the stop ring 124 engages stop member 125 of the backstop 127 preventing accidental distal movement of the protective sleeve 123. Thus, when the sealing apparatus 10 is introduced to a tissue tract, as described in more detail below, movement of the protective sleeve 123 in either the distal or proximal direction is inhibited.

To allow selective proximal retraction of the protective sleeve 123, the key 126 (FIGS. 1 and 2) may be axially advanced to engage the latching element 120, as illustrated in FIG. 3. The key 126 fits inside of the protective sleeve 123 and depresses or radially contracts the latch element 120 so that it fits within the interior circumference of the stop ring 124, thus allowing proximal retraction of the protective sleeve 123, as shown in FIG. 4.

Figure 5:
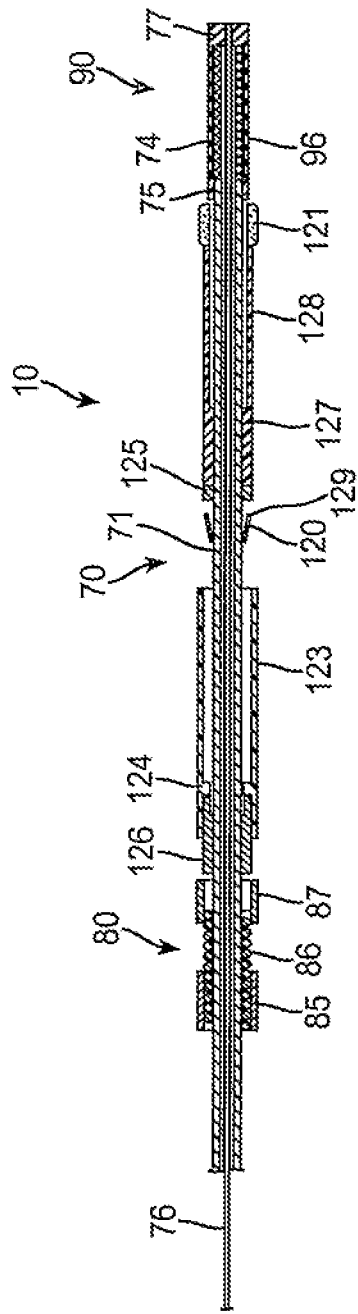
Figure 6:
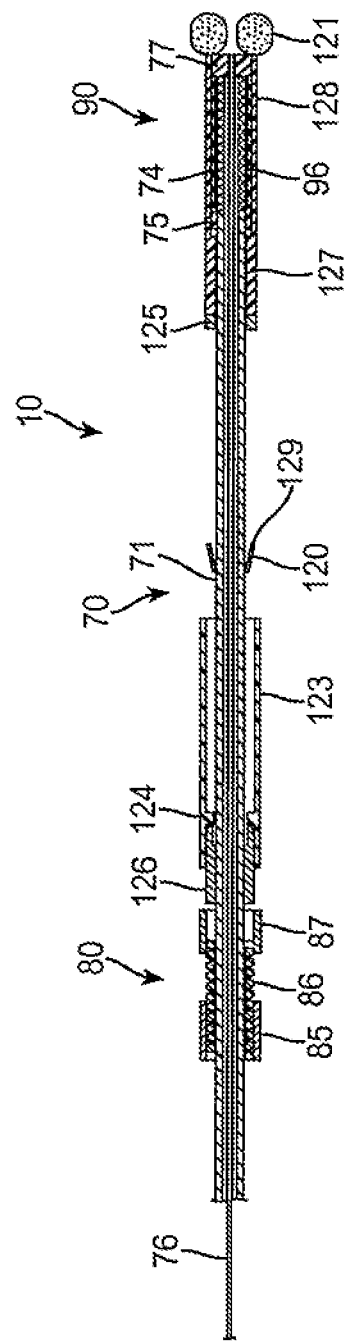
Figure 7:
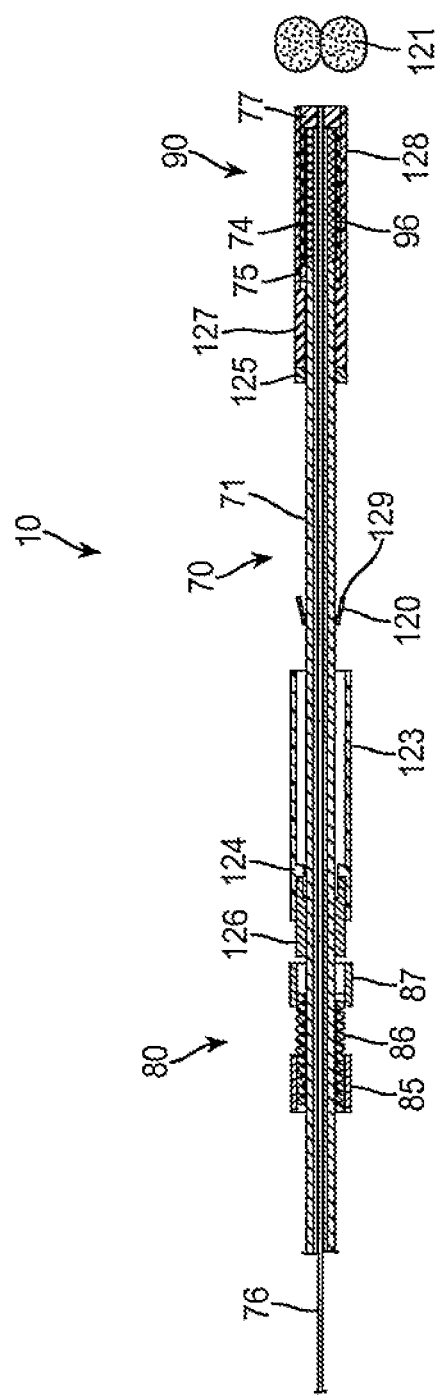

Once the key 126 has engaged and constrained the latch element 120, as shown in FIG. 3, the protective sleeve 123 may be proximally withdrawn past the hemostatic implant 121 and the backstop 127, as shown in FIG. 4. Thus, the hemostatic implant 121 will be released from constraint and exposed to the environment in the tissue tract. The environment in the tissue tract will include blood and other body fluids which can hydrate the hemostatic implant 121, causing swelling as shown in FIG. 4. The swelling will continue, as shown in FIG. 5, and the radially expanded occlusion element 90 can be collapsed using the handle assembly, as shown in FIG. 5. The collapsed occlusion element 90 can then be proximally withdrawn, and the sealing apparatus can be pulled away from the hemostatic implant, as shown in FIG. 7.

Figure 8B:
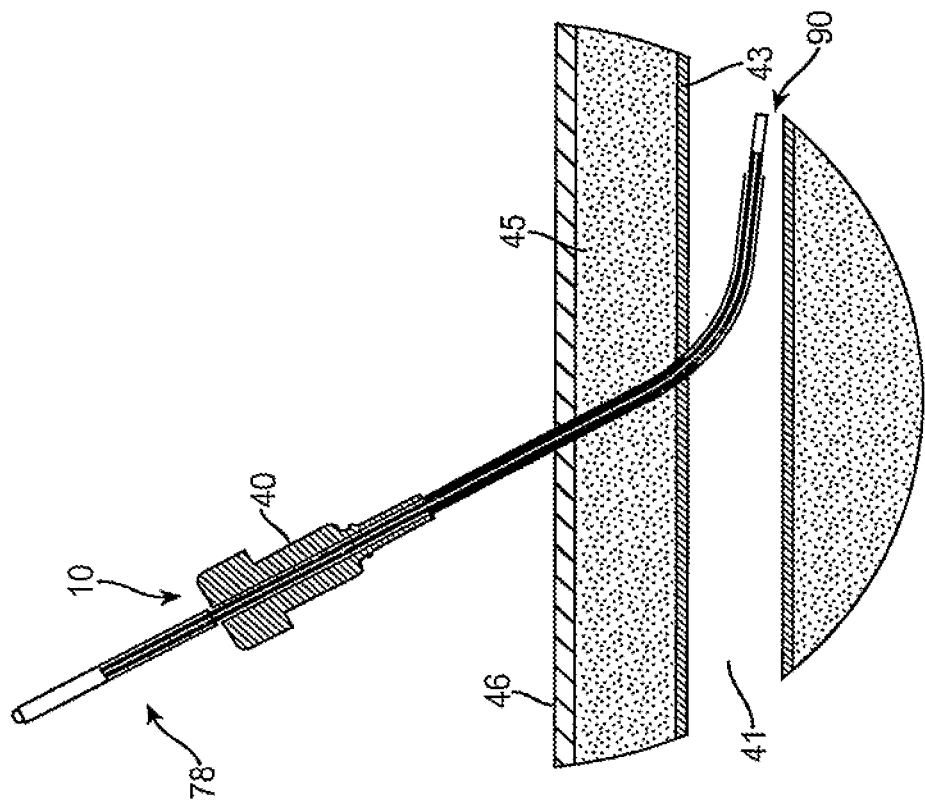
Figure 8A:
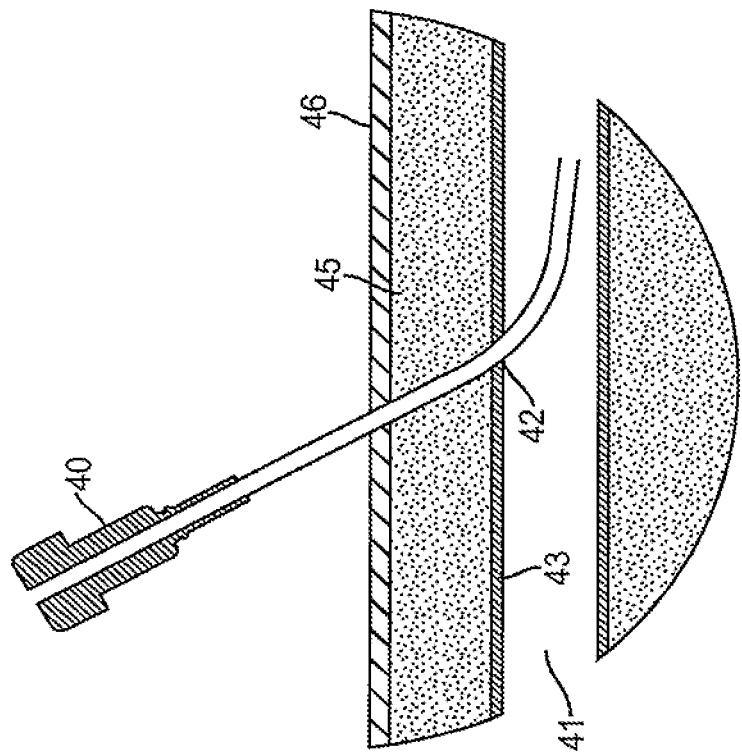

Referring now to FIGS. 8A-8I, deployment and use of the sealing apparatus 10 of the present invention through an introducer or access sheath 40 will be described in more detail. Introducer sheath 40 will typically be in place within a blood vessel lumen 41 passing from the skin surface 46 through tissue 45 in a tissue tract. A vascular wall penetration 42 will thus be present in the vascular wall 43, all as shown in FIG. 8A. The sealing apparatus 10 is then introduced through the access sheath 40 so that the expansible occlusion element 90 passes out through the distal end of the sheath, as shown in FIG. 8B. Handle assembly 78 will remain outside of the sheath and accessible to the user so that the slide assembly 101 may be pulled relative to the cylindrical body 103 to radially expand the occlusion element 90, as shown in FIG. 8C. The vascular access sheath 40 may then be withdrawn over the exterior of the sealing apparatus 10 while the sealing apparatus is simultaneously withdrawn to seat the expanded occlusion element 90 against the vascular penetration 42, as shown in FIG. 8D.

Figure 8I:
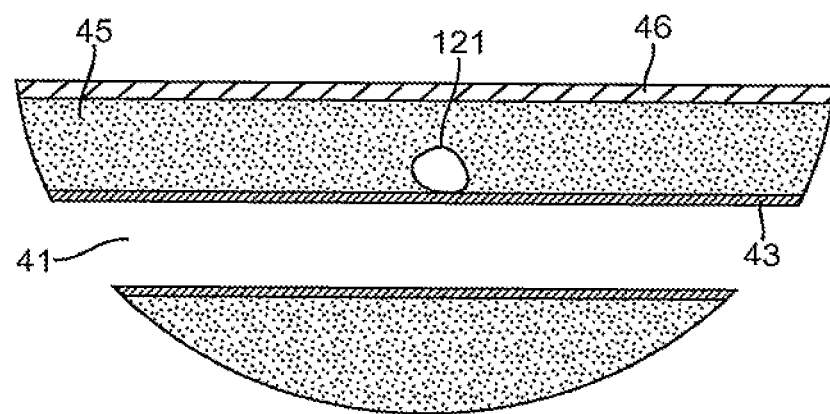

At that point, the protective sleeve 123 and key 126 become exposed and available to the user for manipulation. After optional fluoroscopic verification of the location of the occlusion element 90, the key may then be distally advanced over the outer tube 71 so that the key engages and depresses the latch 120 (FIG. 1A) as illustrated in FIG. 8E. The key 126 and protective sleeve 123 may then be manually pulled in a proximal direction over the outer tube 71 to release the hemostatic implant 121, as shown in FIG. 8F. The expandable element 90 may then be collapsed, as shown in FIG. 8G. The entire sealing apparatus 10, except for the hemostatic implant 121, may then be withdrawn from the tissue tract, leaving the hemostatic implant 121 in place over the now closed vascular wall penetration, as shown in FIG. 8I. The hemostatic implant, which may optionally carry the antiproliferative, coagulation promoting, and/or radiopaque substances, will remain in place inhibiting bleeding and allowing the vascular wall penetration to heal. Over time, the hemostatic implants 121 will preferably biodegrade, leaving a healed tissue tract and vascular wall penetration which are usually suitable for re-entry at a subsequent time.

Figure 9A:
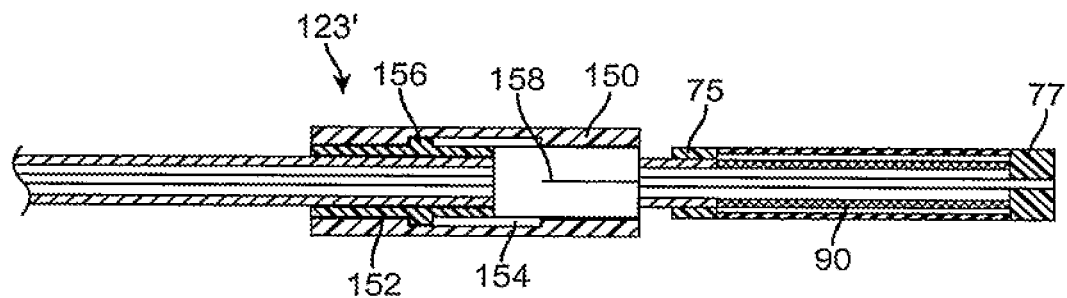
FIGS. 9A-9C illustrate a sealing apparatus in accordance with the present invention having a protective sleeve including an outer sleeve and an inner release sheath.
Figure 9B:
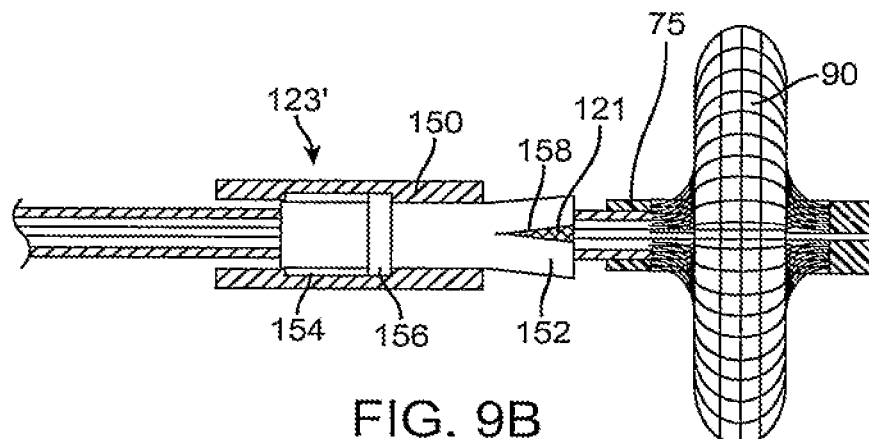
Figure 9C:
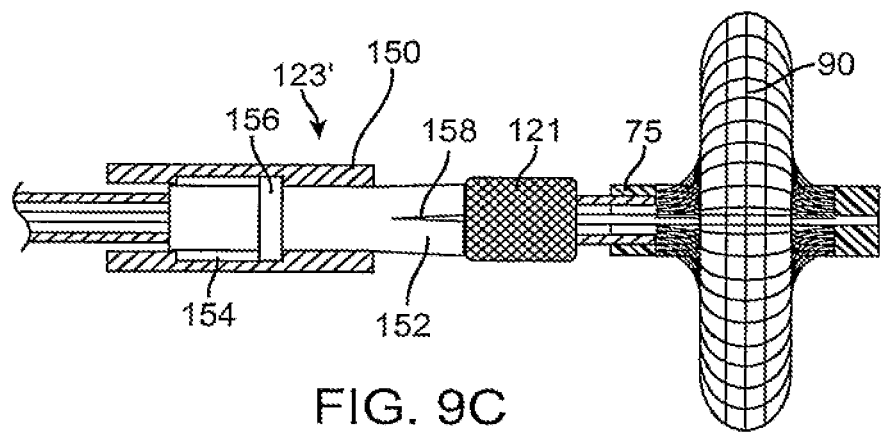

Referring now to FIGS. 9A-9C, a protective sleeve 123' comprises an outer sleeve 150 and an inner release sheath 152. The outer sleeve 150 and inner release sheath 152 are separately retractable so that the outer sleeve may first be retracted relative to the hemostatic implant 121 (FIG. 9B) while the inner release sheath initially remains over the implant. The release sheath 152 will thus provide an anti-friction interface so that the outer sleeve 150 slides over the implant 121 with reduced sticking. The inner release sheath 152 is preferably formed from a relatively lubricious or slippery material and will preferably include an axial opening or slit 158 which permits the distal portion thereof to partially open after the outer sleeve 150 has been retracted, as shown in FIG. 9B. Once the outer sleeve 150 has been retracted to relieve constraint over the hemostatic implant, the inner sleeve may then be retracted to completely release the hemostatic implant, as shown in FIG. 9C. Conveniently, the outer sleeve 150 may be coupled to the inner release sheath 152 so that proximal retraction of the outer sleeve will automatically retract the inner release sheath at the proper point in travel. For example, a cavity or channel 154 may be formed in an inner surface of the outer sleeve 150 and a ring or other engaging element 156 may be formed on the outer surface of the inner release sheath 152. Initially, the ring 156 will be positioned at the proximal end of the cavity or channel 154, as shown in FIG. 9A. After the outer sleeve 150 has been retracted so that it no longer lies over the implant 121, the ring may then engage a distal end of the cavity or channel 154, as shown in FIG. 9B, and engage the ring 156, allowing the outer sleeve to then pull the inner sleeve proximally, as shown in FIG. 9C, to fully release the hemostatic implant 121.

Figure 10A:
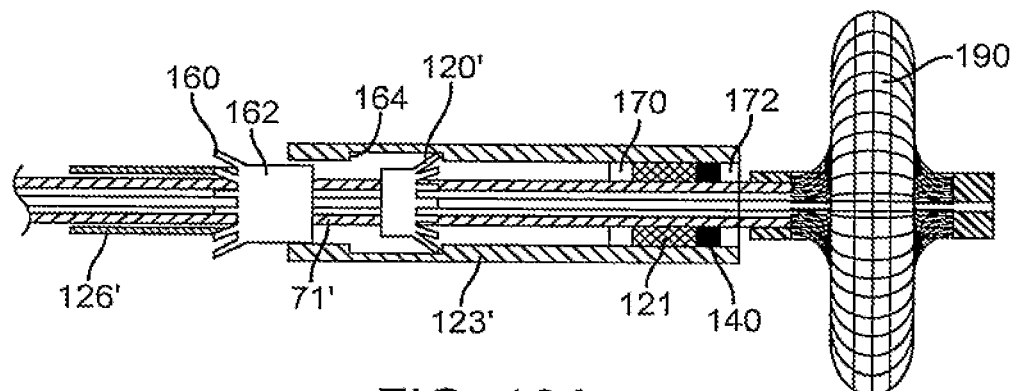
FIGS. 10A-10C illustrate a sealing apparatus in accordance with the present invention having a key latch mechanism which engages the protective sleeve and may be used to proximally withdraw the sleeve to deploy the hemostatic implant.
Figure 10B:
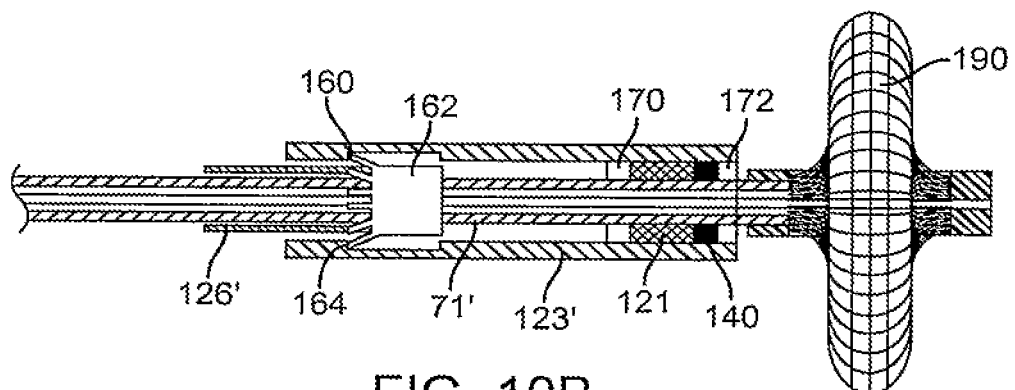
Figure 10C:
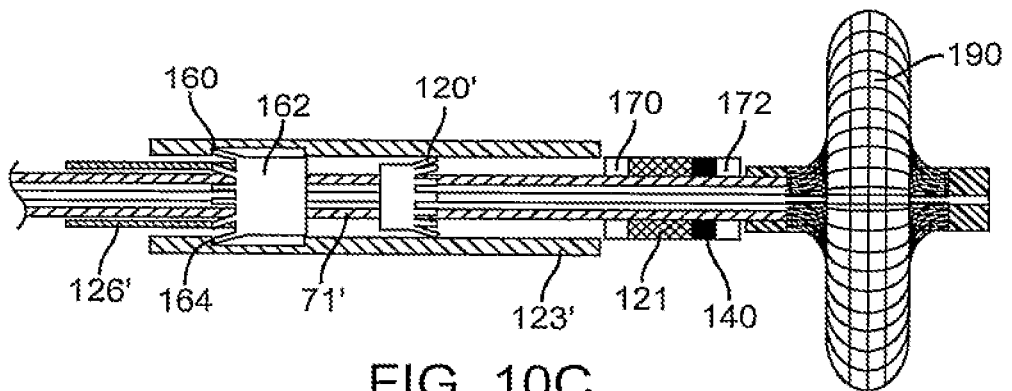

Referring now to FIGS. 10A-10C, it is also possible to selectively couple the key 126' to a protective sleeve 123'. The key 126' has a coupling element, such as plurality of proximally disposed barbs 160 at its distal end. The key 126' may be advanced into the protective sleeve 123' where a distal end 162 of the key 126' engages latching element 120' on the outer tube 71'. Latching mechanism 120' may conveniently comprise a plurality of barbs so that advancement of the key 123' radially closes the barbs allowing the protective sleeve 123' to be proximally retracted relative to the tube 71'. Once the key 126' is fully distally advanced, as shown in FIG. 10B, the proximally disposed barbs 160 will engage an inner lip 164 at the proximal end of the protective sleeve 123'. Thus, as the key 126' is proximally retracted, as shown in FIG. 10C, the key will pull the protective sleeve 123' in a proximal direction, thus exposing the implant 121.

Figure 11A:
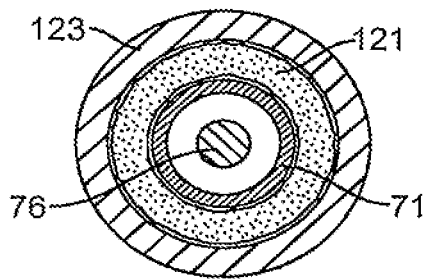
FIGS. 11A and 11B illustrate a hemostatic implant which is coaxially disposed about the shaft of the deployment apparatus of the present invention.
Figure 11B:
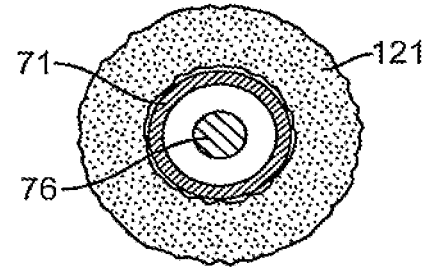

Referring now to FIGS. 11A and 11B, the hemostatic implant 121 may be disposed coaxially over the outer tube 71 and in a rod 76. By proximally retracting the protective sleeve 123, the implant 121 is released and can hydrate as shown in FIG. 11B. As described previously, however, it will still be necessary to withdraw the outer tube 71 as well as the collapsed occlusion element 90 past the hemostatic implant 121. When the hemostatic implant 121 fully circumscribes the outer tube 71, however, both the tube 71 and the collapsed occlusion element 90 can potentially dislodge the implant within the tissue tract.

Figure 12A:
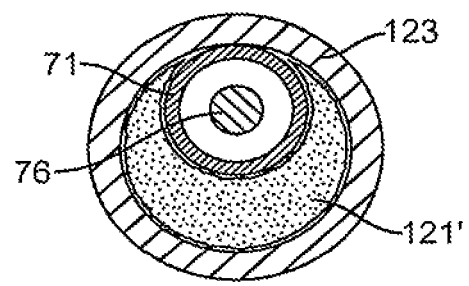
FIGS. 12A and 12B illustrate the hemostatic implant which is laterally disposed relative to the shaft of the deployment mechanism.
Figure 12B:
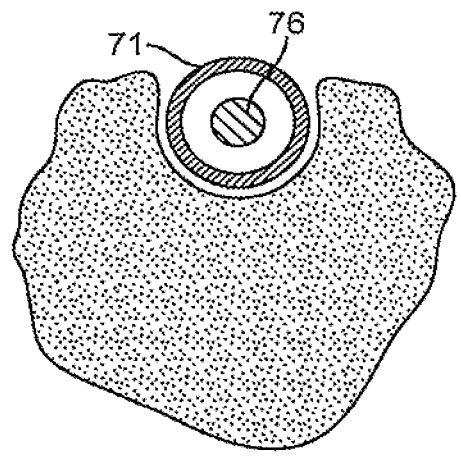

Therefore, in some instances, it will be desirable to modify the geometry of the implant to facilitate withdrawal of the outer tube and the collapsed occlusion element. For example, as shown in FIGS. 12A and 12B, hemostatic implant 121' can be formed with a crescent-shaped cross-section partially or fully circumscribing the outer tube 71 which carries it. By laterally displacing the outer tube 71 and inner rod 76 within the protective sleeve 123, as shown in FIG. 12A, the volume of the hemostatic implant 121 will be generally the same as that shown in FIG. 11A. When the protective sleeve 123 is withdrawn, however, as shown in FIG. 12B, the hemostatic implant 121 will hydrate and expand laterally on one side of the outer tube 71, as shown in FIG. 12B. By disposing the outer tube 71 and collapsed occlusive element 90 to one side of the implant, it is much easier to withdraw the apparatus and collapsed occlusion member past the implant without dislodging the implant within the tissue tract.

Referring now to FIGS. 13A through 13G, use of the vascular closure devices of the present invention, as described above, for closing multiple vascular wall penetrations in a single blood vessel will be described. While this description is made with specific reference to the particular devices described above, it should be appreciated that the methods described for closing multiple vascular wall penetrations can be performed using other vascular closure devices, particularly those which rely on engaging an occlusive or anchoring element at a distal end of a closure device shaft against an inner wall of the blood vessel adjacent to the vascular wall penetration prior to closure. While the methods described and claimed herein are particularly preferred for use with vascular closure devices which place a hemostatic plug at the distal end of a tissue tract above the vascular wall penetration, the methods can also be employed with other sealing protocols, such as catalytically induced clotting, suturing, natural clotting, devices with intravascular implant component, and the like.

Figure 13A:
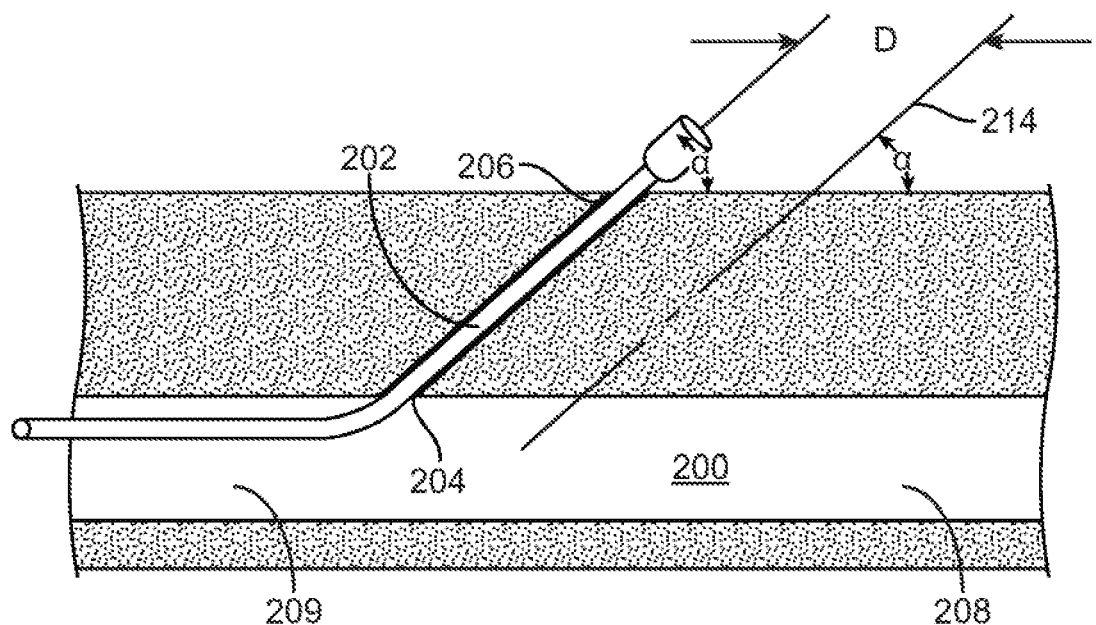
FIGS. 13A-13G illustrate use of two vascular sealing apparatuses for closing two vascular penetrations in a patient vein in accordance with the principles of the present invention.
Figure 13B:
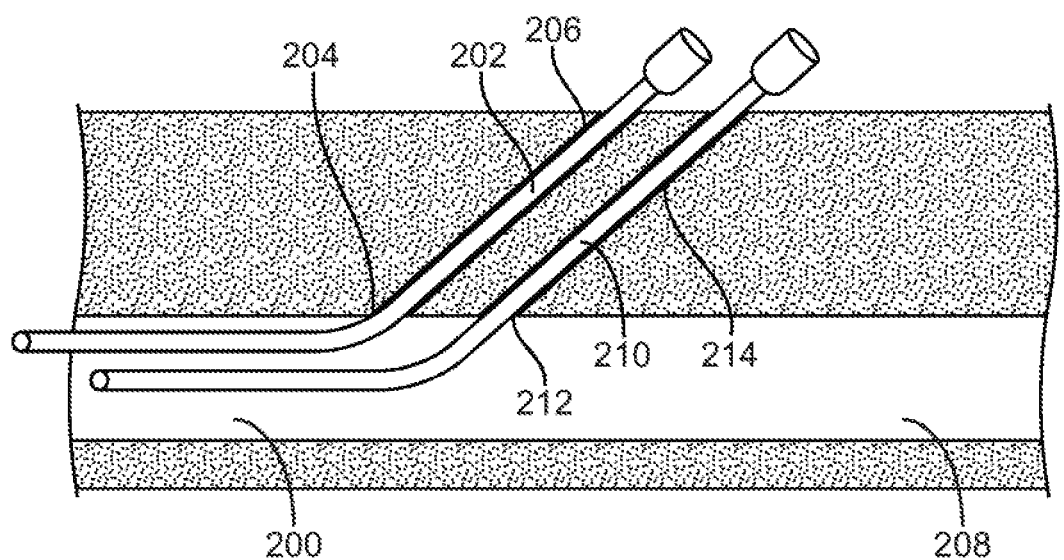

As was explained above, in order to avoid interference of closure devices with each other or interference of a closure device with an adjacent indwelling sheath, a minimum separation is required between the puncture sites in a vessel. Referring now to FIG. 13A, a first tissue tract 206 is formed to gain access to femoral vein 200 at a vascular wall penetration 204 at the distal end of the tissue tract. The first tissue tract 206 is formed at an angle α relative to a caudal segment 208 of the femoral vein 200. The angle α will be acute, typically in the range from 30° to 60°, but the exact angle of the first tissue tract 206 is not critical.

A second tissue tract 214 is then formed at a second location to provide a second access path to the femoral vein 200. The second location may be above or below the first tissue tract 206. In this example tissue tract 214 is formed in a caudal direction relative to the first tissue tract 206, as shown in FIG. 13A. In order to achieve a desired separation between the puncture sites in the vessel wall, the separation is first established on the skin surface and the second tissue tract is formed at the same angle as the first tissue tract relative to the vessel. The angle α of the second tissue tract 214 should be made as close as possible to the angle α of the first tissue tract so that the tissue tracts will be parallel to one another or as closely parallel as possible. After the second tissue tract 214 is formed, it will be appreciated that the first tissue tract 206 is in a cephalad direction relative to the second tissue tract 214 and that the separation distance between the puncture sites 204 and 212 in the vessel would be similar to that of the puncture sites at the skin level. As both tissue tracts 206 and 214 are inclined relative to the femoral vein 208 in the caudal direction, it will be appreciated that the first access sheath 202, when inserted, will lie over the second tissue tract 214, as well as the second access sheath 210 which is introduced (as described below), thus potentially attenuating or obscuring any imaging of the second tissue tract in an anterior-posterior (AP) direction.

Referring now to FIGS. 13A and B, the first access sheath 202 is placed through the first tissue tract 206 and a vascular wall penetration 204 at the distal end of tissue tract 206. The second access sheath 210 is introduced through the second tissue tract 214 so that it extends through a second vascular wall penetration 212 and into the lumen of the femoral vein 200. Additional access sheaths (not illustrated) may be introduced in a similar manner. Each access sheath is potentially obscured from fluoroscopic or other visualization by the other access sheath(s) in the cephalad direction. Once two, three, four, or more access sheaths, as needed for a particular procedure, are in place, the procedure may be performed through these access sheaths in a conventional manner. The use of multiple access sheaths in a femoral vein is appropriate for performing cardiac procedures, and in particular cardiac ablation, cardiac mapping and similar cardiac procedures.

Figure 13C:
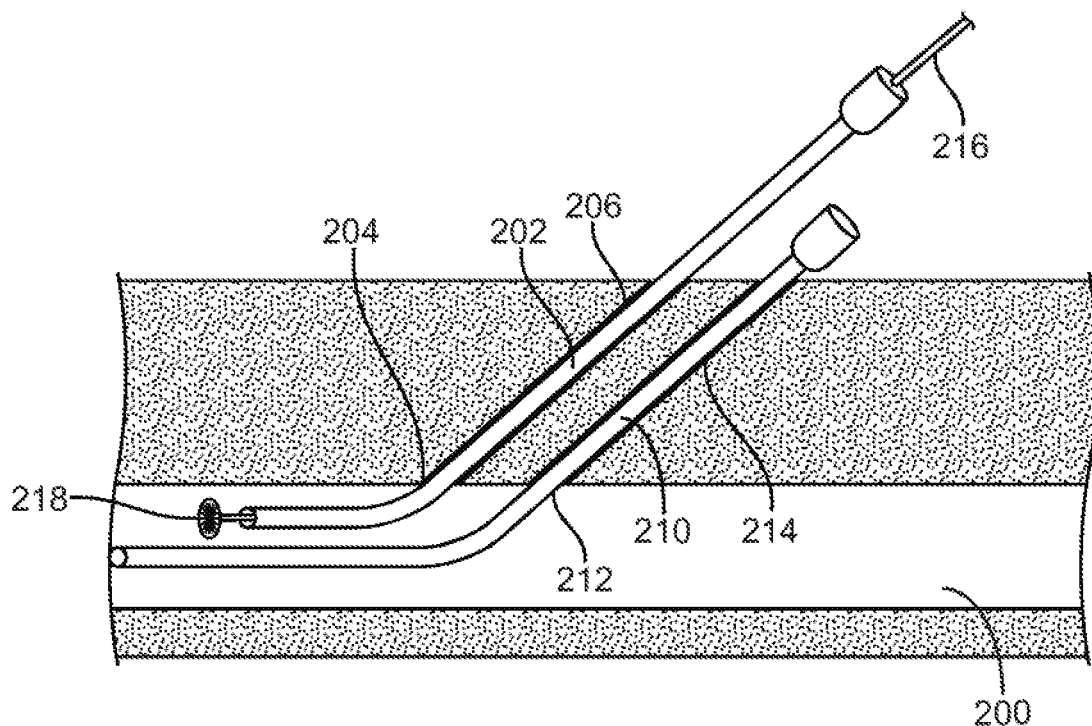
Figure 13D:
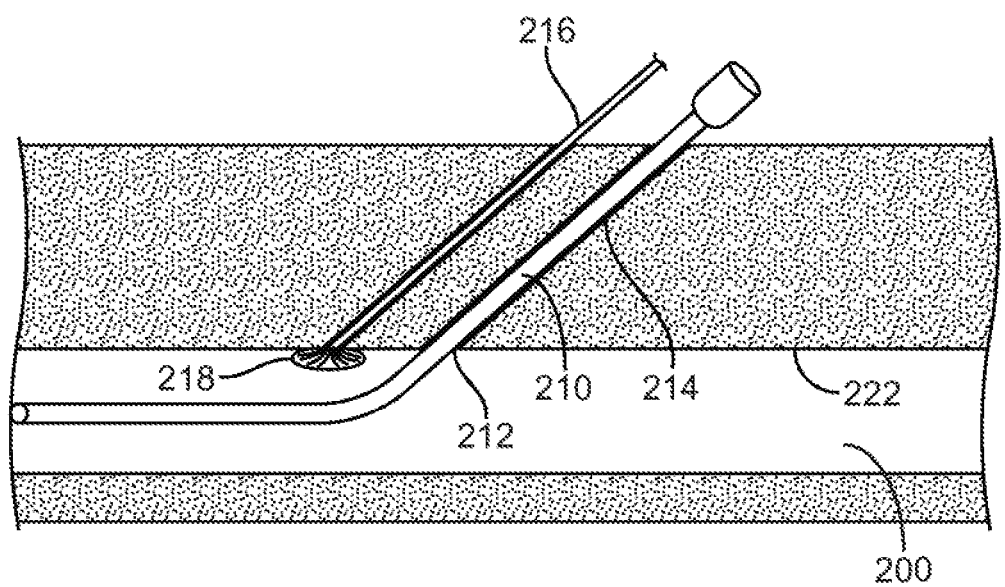

Once the desired cardiac or other procedures are completed, and the working catheters removed, it will be necessary to remove the access sheaths and seal the vascular wall penetrations in accordance with the principles of the present invention. As shown in FIG. 13C, and as was explained above, in order to obtain a more enhanced fluoroscopic and/or ultrasonic image of the closure device during the deployment process, the most cephalad vascular penetration is closed first. Vascular penetration 204 at the distal end of the first tissue tract 206 will be closed first using a first vascular closure device 216 having an expandable occlusion element 218 at its distal end. In order to avoid the interference of the deployed expandable occlusion element 218 of the closure device 216 with the distal end of the indwelling sheath 214, it is preferred that the access sheath 202 be partially withdrawn prior to insertion of the closure device. Access sheath 202 is retracted so that a distal end of the sheath is drawn inwardly past a distal end of the second access sheath 210. By deploying the first occlusion element 218 above the body of the second access sheath 210, interference between the distal end of the second access sheath and the deployed first occlusion element 218 is avoided. The vascular closure device 216 is then introduced through a lumen of the first access sheath 202, and the first occlusion element 218 is expanded within the lumen of the femoral vein 200. Occlusion device 216 is retracted to draw the deployed first occlusion element 218 against the inner wall 222 of the femoral vein 200. The position of the occlusion element 218 may be verified by imaging free from interference of an indwelling sheath. Referring to FIG. 13D, it is also appreciated that the method of forming multiple vascular penetrations in the vessel wall with a minimum separation distance, as was described above, eliminated the interference of the deployed expandable member 218 with the indwelling sheath 214.

Figure 13E:
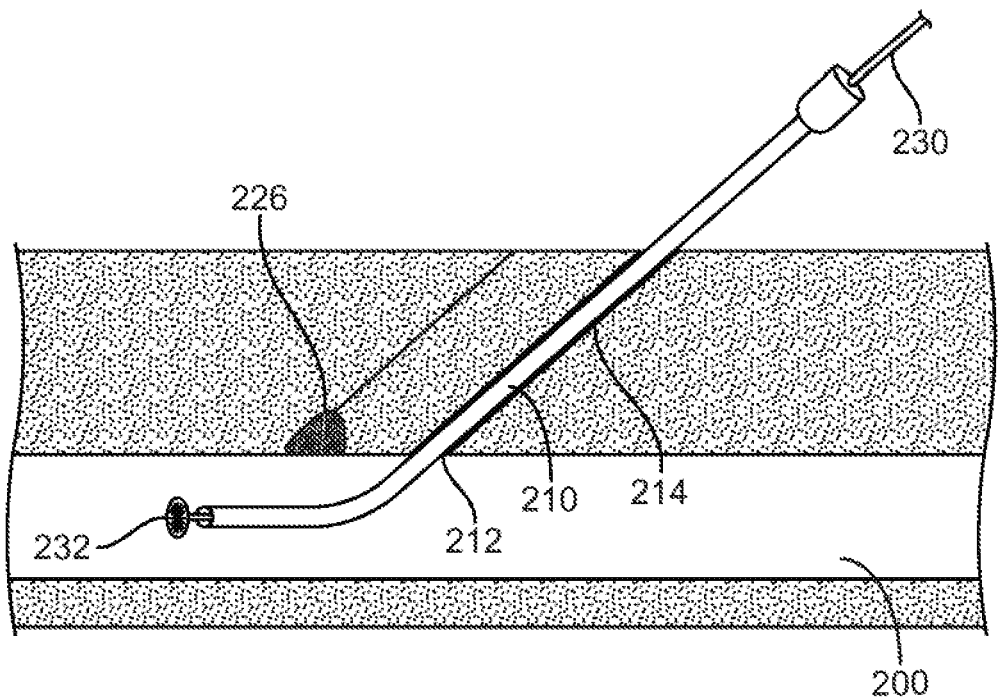

Referring now to FIGS. 13D and 13E, a hemostatic plug 226 may be introduced using the vascular closure device 216 in a manner as described in detail in earlier portions of this application. The first occlusion element 218 may be collapsed and withdrawn through the first hemostatic plug 226, leaving the hemostatic 226 in place and the tissue tract generally closed above it, as shown in FIG. 13E.

Once the first tissue tract 206 has been closed with the hemostatic plug 226 in place, as shown in FIG. 13E, the second vascular closure device 230 having a second occlusion element 232 at its distal end may be imaged as it is deployed to close the second tissue tract 214. It will be appreciated that removal of the first access sheath 202 helps clears a field for fluoroscopic or other imaging of the second vascular closure device 230. It will be further appreciated that even if third, fourth, and other access sheaths are in place, so long as those additional access sheaths are placed in a caudal direction relative to the second access sheath, the second access sheath and its associated vascular closure device will remain available for unobstructed fluoroscopic, ultrasonic or other imaging.

Figure 13F:
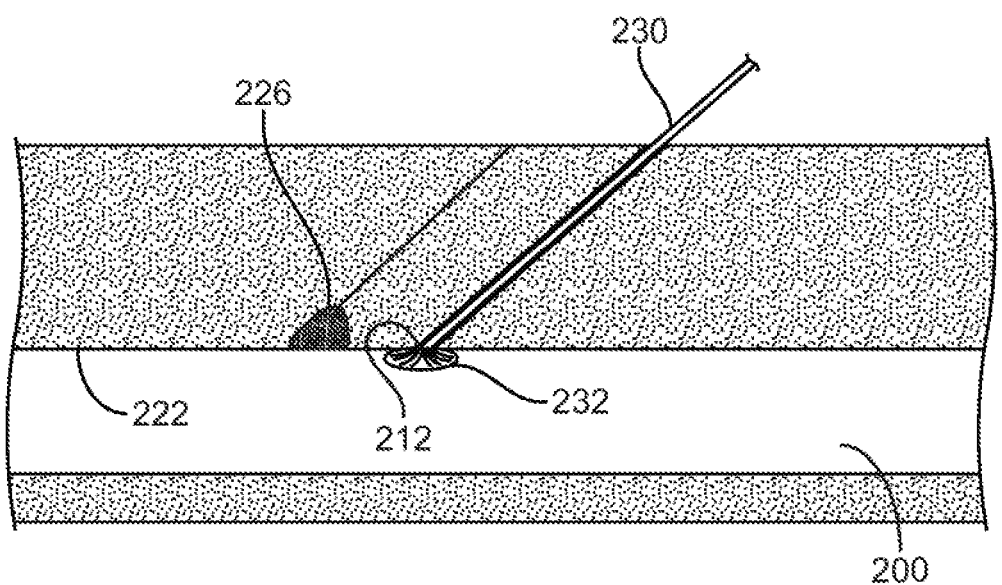
Figure 13G:
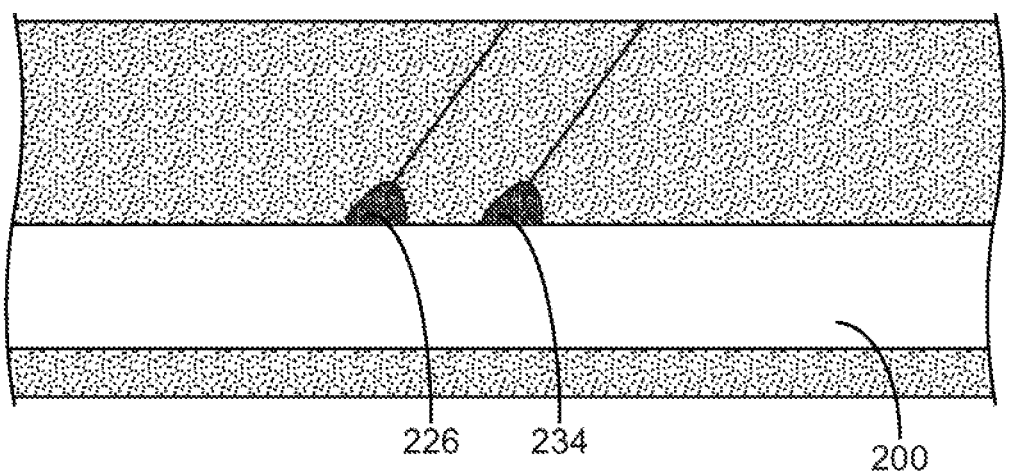

As shown in FIG. 13F, the second occlusion element 232 has been deployed and retracted so that it engages the inner wall 222 of the femoral vein 200 in a manner similar to the first occlusion element 218. A second hemostatic plug 234 may then be deployed using the second vascular closure device 230 as described previously and the second vascular closure device removed, as shown in FIG. 13G. If additional access sheaths had been utilized in the procedure, they may be imaged and closed using the identical protocols as just described.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for forming and closing a plurality of penetrations in a blood vessel, said method comprising:
   forming a cephalad tissue tract from a skin surface to a lumen of a blood vessel, the cephalad tissue tract defining a cephalad penetration in the blood vessel;
   forming a caudal tissue tract from the skin surface to the lumen of the blood vessel, the caudal tissue tract defining a caudal penetration in the blood vessel, wherein the cephalad penetration is positioned along the blood vessel at a location closer to a head of a patient than is the caudal penetration;

placing a cephalad sheath through the cephalad tissue tract into the lumen of the blood vessel;

placing a caudal sheath through the caudal tissue tract into the lumen of the blood vessel, wherein a portion of the cephalad sheath lies between a portion of the caudal sheath and the skin surface;

performing a diagnostic or an interventional procedure with catheters placed through the cephalad sheath and the caudal sheath;

removing the catheters from the sheaths;

positioning a distal region of a cephalad closure device through the cephalad penetration into the blood vessel lumen, wherein the caudal sheath does not mask imaging of the distal region of the cephalad closure device;

closing the cephalad penetration with the cephalad closure device positioned through the cephalad sheath;

positioning a distal region of a caudal closure device thorough the caudal penetration into the lumen of the blood vessel; and closing the caudal penetration with the caudal closure device positioned through the caudal sheath.

2. The method as in claim 1, wherein the cephalad and caudal tissue tracts are formed along parallel paths from the skin surface to the blood vessel lumen.

3. The method as in claim 2, wherein the parallel paths have a minimum spacing along a cephalad-caudal axis equal to the sum of (1) one-half of a deployed length or diameter of the occlusion element and (2) one-half a diameter of the access sheath.

4. The method of claim 2, wherein the parallel paths are spaced apart along the cephalad-caudal axis by at least a full length or a full diameter of the occlusion element.

5. The method as in claim 2, wherein the parallel paths are axially spaced apart by a distance in the range from 0.5 cm to 1 cm.

6. The method as in claim 2, wherein the blood vessel is a femoral vein and parallel paths are deployed at an acute angle relative to an upstream segment of the femoral vein.

7. The method as in claim 6, wherein the acute angle is in the range from 30° to 60°.

8. The method as in claim 2, wherein the blood vessel is a femoral artery and parallel paths are deployed at an acute angle relative to a downstream segment of the femoral artery.

9. The method as in claim 8, wherein the acute angle is in the range from 30° to 60°.

10. The method as in claim 1, wherein the penetration in the cephalad tissue tract is closed and the cephalad closure device is withdrawn prior to introducing the caudal vascular closure device through the caudal sheath.

11. The method as in claim 1, further comprising:
forming a third tissue tract on a caudal side of the caudal tissue tract before performing the diagnostic or interventional procedure, the third tissue tract defining a third penetration;

placing a third sheath through the third tissue tract and into the lumen of the blood vessel before performing the diagnostic or interventional procedure;

positioning a distal region of a third closure device in the lumen of the blood vessel after performing the diagnostic or interventional procedure; and closing the third penetration with the third closure device positioned through the third sheath;

wherein the caudal penetration is closed and the caudal closure device is withdrawn prior to introducing the third closure device into the third sheath.

12. The method as in claim 11, wherein the third penetration is closed and the third closure device is withdrawn prior to sealing a fourth vascular access penetration.

13. The method as in claim 1, wherein the cephalad sheath is partially withdrawn before the insertion of the cephalad closure device.

14. The method of claim 1 wherein the cephalad closure device and the caudal sheath are configured to be imaged after removal of the cephalad sheath.

15. The method as in claim 1, wherein closing comprises releasing a hemostatic plug from the distal region of the vascular closure device over the penetration.

16. The method as in claim 1, wherein imaging the blood vessel lumen comprises fluoroscopically or ultrasonically imaging the blood vessel lumen.

17. The method as in claim 1, wherein withdrawal of the cephalad sheath and cephalad closure device exposes the caudal sheath and caudal closure device for imaging.

18. The method as in claim 1, wherein the cephalad closure device and the caudal closure device each include an occlusion element, the occlusion elements being deployed and the cephalad sheath and the caudal sheath are removed prior to sealing the cephalad penetration and the caudal penetration.

19. The method as in claim 18, wherein the cephalad closure device and the caudal closure device are configured to be imaged after removal of the cephalad sheath and the caudal sheath.

20. The method as in claim 1, wherein the therapeutic or diagnostic procedure comprises a cardiac procedure.

21. The method as in claim 1, further comprising imaging the blood vessel lumen after introducing the cephalad closure device through the cephalad sheath and before closing the cephalad penetration with the cephalad closure device.

22. A method, comprising:
positioning, after performance of a diagnostic or an interventional procedure, a distal end of a cephalad closure device through a cephalad penetration defined in a blood vessel, the cephalad penetration being disposed at the end of a cephalad tissue tract that is formed from a skin surface to a lumen of the blood vessel;

further positioning the cephalad closure device such that once an occlusion element of the cephalad closure device is deployed, the occlusion element lies caudal to the distal end of the caudal sheath;

closing the cephalad penetration with the occlusion element disposed at the distal end of the cephalad closure device;

positioning, after performance of the diagnostic or the interventional procedure, a distal end of a caudal closure device through a caudal penetration defined in a blood vessel, the caudal penetration being at the end of a caudal tissue tract that is formed from the skin surface to the lumen of the blood vessel; and closing the caudal penetration with an occlusion element disposed at the distal end of the caudal closure device.

23. The method as in claim 22, wherein the cephalad and caudal tissue tracts are formed along parallel paths from the skin surface to the blood vessel lumen.

24. The method as in claim 23, wherein the parallel paths have a minimum spacing along a cephalad-caudal axis equal to the sum of (1) one-half of a deployed length or diameter of an occlusion element of one of the closure devices and (2) one-half a diameter of the sheath.

25. The method of claim 23, wherein the parallel paths are spaced apart along the cephalad-caudal axis by at least a full length or a full diameter of the occlusion element.

26. The method as in claim 23, wherein the parallel paths are axially spaced apart by a distance in the range from 0.5 cm to 1 cm.

27. The method as in claim 23, wherein the blood vessel is a femoral vein and parallel paths are deployed at an acute angle relative to an upstream segment of the femoral vein.

28. The method as in claim 27, wherein the acute angle is in the range from 30° to 60°.

29. The method as in claim 23, wherein the blood vessel is a femoral artery and parallel paths are deployed at an acute angle relative to a downstream segment of the femoral artery.

30. The method as in claim 29, wherein the acute angle is in the range from 30° to 60°.

31. The method as in claim 22, wherein the cephalad penetration is closed and the cephalad closure device is withdrawn prior to positioning the distal end of the caudal closure device through the caudal penetration.

32. The method as in claim 22, wherein closing comprises releasing a hemostatic plug from the distal region of the closure device over the penetration.

33. The method as in claim 22, wherein the cephalad closure device and the caudal closure device each include an occlusion element, the occlusion elements being deployed and the cephalad sheath and the caudal sheath are removed prior to sealing the cephalad penetration and the caudal penetration.

34. The method as in claim 33, wherein the cephalad closure device and the caudal closure device are configured to be imaged.

35. The method as in claim 22, further comprising imaging the blood vessel lumen after introducing the cephalad closure device through the cephalad sheath and before closing the cephalad penetration with the cephalad closure device.

36. The method as in claim 22, wherein the therapeutic or diagnostic procedure comprises a cardiac procedure.

\* \* \* \* \*